(12) United States Patent
Pourmand et al.

(10) Patent No.: US 8,313,907 B2
(45) Date of Patent: *Nov. 20, 2012

(54) CHARGE PERTURBATION DETECTION SYSTEM FOR DNA AND OTHER MOLECULES

(75) Inventors: Nader Pourmand, Scotts Valley, CA (US); Miloslav Karhanek, Santa Cruz, CA (US); Ronald W. Davis, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/170,607

(22) Filed: Jun. 28, 2011

(65) Prior Publication Data
US 2011/0281739 A1    Nov. 17, 2011

Related U.S. Application Data

(63) Continuation of application No. 12/821,809, filed on Jun. 23, 2010, now Pat. No. 8,012,756, which is a continuation of application No. 11/271,678, filed on Nov. 10, 2005, now Pat. No. 7,785,785.

(60) Provisional application No. 60/627,192, filed on Nov. 12, 2004.

(51) Int. Cl.
*C12Q 1/68*    (2006.01)
*C12P 19/34*   (2006.01)
*C07H 21/04*   (2006.01)
*G01C 15/06*   (2006.01)

(52) U.S. Cl. ............... 435/6.1; 435/91.1; 435/283.1; 422/82.01; 536/23.1

(58) Field of Classification Search ............... None
See application file for complete search history.

(56) References Cited

U.S. PATENT DOCUMENTS

| 4,490,216 A | 12/1984 | McConnell |
| 5,164,319 A | 11/1992 | Hafeman et al. |
| 5,192,507 A | 3/1993 | Taylor et al. |

(Continued)

OTHER PUBLICATIONS

Nader Pourmand, et al., "Multiplex Pyrosequencing," Nucleic Acids Research, 2002, vol. 30, No. 7 e31.

(Continued)

*Primary Examiner* — Betty Forman
(74) *Attorney, Agent, or Firm* — David J. Aston; Peters Verny, LLP

(57) ABSTRACT

Methods and apparatus for direct detection of chemical reactions are provided. In a preferred embodiment, electric charge perturbations of the local environment during enzyme-catalyzed reactions are sensed by an electrode system with an immobilized target molecule. The target molecule is preferably DNA. The charge perturbation caused by the polymerase reaction can uniquely identify a DNA sequence. The polymerization process generates local perturbations of charge in the solution near the electrode surface and induces a charge in a polarazible gold electrode. This event is detected as a transient current by a voltage clamp amplifier. Detection of single nucleotides in a sequence can be determined by dispensing individual dNTPs to the electrode solution and detecting the charge perturbations. Alternatively, multiple bases can be determined at the same time using a mix of all dNTPs with subsequent analysis of the resulting signal. The initial enzyme attachment to the DNA molecule can be detected prior to polymerization, with electrode capacitance measurement using the same voltage-clamp amplifier. This technique and device may be adapted to other reaction determinations, such as enzymatic reactions, other electrode configurations, and other amplifying circuits.

8 Claims, 8 Drawing Sheets

U.S. PATENT DOCUMENTS

| | | | |
|---|---|---|---|
| 5,466,348 | A | 11/1995 | Holm-Kennedy |
| 5,500,188 | A | 3/1996 | Hafeman et al. |
| 5,521,101 | A | 5/1996 | Saini et al. |
| 5,540,828 | A | 7/1996 | Yacynych |
| 5,955,379 | A | 9/1999 | Lennox et al. |
| 6,100,045 | A | 8/2000 | Van Es |
| 6,322,963 | B1 | 11/2001 | Bauer |
| 6,391,558 | B1 | 5/2002 | Henkens et al. |
| 6,468,785 | B1 | 10/2002 | Wang et al. |
| 6,518,024 | B2 | 2/2003 | Choong et al. |
| 6,762,050 | B2 | 7/2004 | Fukushima et al. |
| 7,125,478 | B2 * | 10/2006 | Selvaganapathy et al. ... 204/452 |
| 7,223,540 | B2 | 5/2007 | Pourmand et al. |
| 7,785,785 | B2 | 8/2010 | Pourmand |
| 8,012,756 | B2 | 9/2011 | Pourmand |
| 2002/0012933 | A1 | 1/2002 | Rothberg et al. |
| 2002/0039743 | A1 | 4/2002 | Hashimoto et al. |
| 2002/0090649 | A1 | 7/2002 | Chan et al. |
| 2002/0123048 | A1 | 9/2002 | Gau |
| 2002/0155476 | A1 | 10/2002 | Pourmand et al. |
| 2003/0082583 | A1 | 5/2003 | Hassibi et al. |
| 2004/0197793 | A1 | 10/2004 | Hassibi et al. |
| 2005/0009022 | A1 | 1/2005 | Weiner et al. |
| 2005/0084851 | A1 | 4/2005 | Ronaghi et al. |
| 2005/0123937 | A1 | 6/2005 | Thorp et al. |
| 2006/0105373 | A1 | 5/2006 | Pourmand et al. |
| 2007/0181466 | A1 | 8/2007 | Wang et al. |
| 2009/0104707 | A1 | 4/2009 | Wang et al. |
| 2010/0075340 | A1 | 3/2010 | Javanmard et al. |

OTHER PUBLICATIONS

Hsueh-Wei Chang, et al., "Detection of Allelic Imbalance in Ascitic Supernatant by Digital Single Nucleotide Polymorphism Analysis," Clinical Cancer Research, Aug. 2002, 2580-2585, vol. 8.

Marcel Margulies, et al., "Genome sequencing in microfabricated high-density picolitre reactors," Nature, Jul. 31, 2005.

T. Gregory Drummond, et al., "Electrochemical DNA sensors," Nature Biotechnology, Oct. 2003, 1192-1199, vol. 21, No. 10.

R. P. Gupta, et al., "YBCO-FET room temperature ammonia sensor," Sensors and Actuators B, 2000, 35-41.

Lowe, "An introduction to the concepts and technology of biosensors," Biosensors, 1985, 1, 3-16.

Fritz, et al., "Electronic detection of DNA by its intrinsic molecular charge", Proceedings of the National Academy of Sciences, 2002, 99: 14142-14146.

Pourmand, et al., "Direct electrical detection of DNA synthesis", Proceedings of the National Academy of Sciences, 2006, 103: 6466-6470.

Int'l Appl. No. PCT/US05/40558, International Search Report dated Dec. 20, 2007, Section C indicating references cited previously.

Int'l Appl. No. PCT/US05/40558, International Search Report dated Nov. 23, 2007, Section C indicating "No references".

Daniels and Pourmand, "Label-Free Impedance Biosensors: Opportunities and Challenges", Electroanalysis, May 16, 2007, 19(12): 1239-1257.

Stefano Cagnin, et al., "Overview of Electrochemical DNA Biosensors: New Approaches to Detect the Expression of Life", Sensors, 2009, 9: 3122-3148.

* cited by examiner

A

B

C

CHARGE PERTURBATION DETECTION SYSTEM FOR DNA AND OTHER MOLECULES

CROSS-REFERENCE TO RELATED APPLICATIONS

This application is a continuation of U.S. patent application Ser. No. 12/821,809 filed on Jun. 23, 2010, now U.S. Pat. No. 8,012,756, which is a continuation of U.S. patent application Ser. No. 11/271,678 filed on Nov. 10, 2005, now U.S. Pat. No. 7,785,785, which claims priority from U.S. Provisional Patent Application No. 60/627,192 filed on Nov. 12, 2004, all of which are hereby incorporated by reference in their entirety.

STATEMENT OF GOVERNMENTAL SUPPORT

This invention was made with Government support under contracts AI059499 and HG000205 awarded by the National Institutes of Health. The Government has certain rights in this invention.

REFERENCE TO SEQUENCE LISTING OR CD ROM

Applicants submit herewith a sequence listing in an ASCII text file (3815_10_3_seq_list.txt), as provided in EFS Legal Framework Notice 20 May 2010, part I-I-1. The file was created Jun. 23, 2011 and contains 703 bytes. Applicants incorporate the contents of the sequence listing by reference in its entirety.

BACKGROUND OF THE INVENTION

1. Field of the Invention

The present invention relates to the field of electrochemical molecular detection, such as the detection of nucleic acid polymerization, by detection of a charged particle (e.g. proton) by means of a sensitive electrical circuit. The present invention has particular application to nucleic acid sequence detection and enzyme substrate modification detection.

2. Related Art

Rapid, sequence-specific DNA detection is essential for applications in medical diagnostics and genetic screening. Electrochemical biosensors that use immobilized nucleic acids are especially promising in these applications because of their potential for miniaturization and automation. Current DNA detection methods based on hybridization rely on various optical, electrochemical or mass readouts. (Refs. 1, 2) However, direct, label-free electrochemical detection methods are not available.

A variety of electrochemical methods have been described, all of which detect direct electronic signals using various electrochemical reactions during DNA hybridization at the electrode surface. (Refs. 1, 2, 6) In contrast, current detection and sequencing-by-synthesis technique requires the use of several enzymatic and photochemical steps. (Refs. 7, 8) Thus a direct electrochemical detection method for this technique would greatly simplify the detection process and accelerate its implementation for rapid DNA sequencing and diagnostics. Described below is a label-free electrochemical detection method, Charge Perturbation Detection (CPD), applied to sequencing-by-synthesis.

3. Discussion of Related Publications and Patents

Drummond, T. G., M. G. Hill, J. K. Barton, "Electrochemical DNA sensors," Nat. Biotechnol. October; 21(10):1192-9 (2003) report direct electrochemical techniques based on detection of electronic signals of electrochemical reactions of DNA or reporter molecules or enzymes recruited to the electrode surface by specific DNA probe-target interactions.

Ronaghi, M. "Pyrosequencing sheds light on DNA sequencing," Genome Res. Ian; 11 (1):3-11 (2001) discloses pyrosequencing detection methods using a bioluminometric detection in a three step reporter technique. The ultimate goal of these efforts is to discriminate individual nucleotides in a DNA molecule. Almost all these techniques use more than one-step electrochemical reaction to produce electronic signal. The CPD (Charge perturbation detection) method and device described below in contrast uses only one-step polymerase-catalyzed reaction to generate an electronic signal detecting a DNA nucleotide or sequence.

Pourmand et al. US 2002/0155476, published Oct. 24, 2002, describes a device for detecting a transient electrical signal in a sample. This device relies on a change in the potential difference between two electrodes when ions are added to a medium contacting the electrodes. A differential amplifier subtracts voltages from the two electrodes to produce the signal. The signal is generated in response to an electric field generated by the migration of ions towards the binding sites on one electrode, as shown in FIG. 2.3 of the publication.

BRIEF SUMMARY OF THE INVENTION

The invention comprises a method and device for direct electrochemical detection of enzymatically catalyzed DNA synthesis by induced surface charge perturbation. Incorporation of a complementary nucleotide triphosphate (NTP) such as deoxynucleotide triphosphate (dNTP) into a self-primed single-stranded DNA attached to the surface of a high overpotential metal (e.g. gold) electrode evokes an electrode surface charge perturbation. This event can be detected as a transient current by a feed back (e.g. voltage-clamp) amplifier.

Based on current understanding of polarizable interfaces (Refs 3, 4) and without wishing to be bound by scientific theory, it is thought that the electrode detects the proton removal from the 3'-hydroxyl group of the DNA molecule during phosphodiester bond formation. (Ref 5).

Thus the present invention provides a device for detecting a chemical reaction of a selected reactant with a target molecule, wherein the reaction produces a charge perturbation on the target molecule. It need not be limited to DNA or other nucleic acid polymerization reactions. The chemical reaction may further provide structural information, such as a DNA or RNA sequence. It may provide information about the state of phosphorylation of a substrate, etc. The device comprises a container for containing reaction medium having therein reactants and target molecules. The container may be a well or a channel; the target molecules (e.g. DNA) may be chemically linked to the electrode, or simply in suspension near the electrode. Since the detection zone in the preferred embodiment has been determined to be about 30 µm, the container should be scaled accordingly. The device further comprises a polarizable electrode in the container adjacent the target molecules. The electrode becomes polarized due to charge perturbation in the reaction mixture and target molecule. Further, an amplifying circuit for maintaining a set potential in the electrode and generating a signal in response to said charge perturbation; and a detector for detecting the signal, thereby indicating reaction of the selected reactant with the target molecule are provided. A voltage clamp amplifier is exemplified as providing sensitivity to very small charge differences.

The device preferably comprises an amplifying circuit with a differential feedback amplifier having one input at a fixed voltage outside the container and another input attached to the electrode.

The amplifying circuit preferably has its negative input connected to the electrode, and the electrode is preferably gold, copper or silver.

The device may further comprise a self-assembled monolayer on the surface of the electrode, for providing insulation, which will facilitate polarization of the electrode. The self-assembled monolayer is preferably linked to the target molecule, so that the charge perturbations on the target molecule occur within a zone that is detectible by the electrode.

As stated, in the preferred device, the electrode is insulated, and the target molecule is a polynucleic acid (e.g. DNA or RNA) linked to the polarizable electrode. The device may be fabricated as an array of a large number of reaction electrodes, each with a different target molecule (e.g. DNA template). This device comprises an addressable array of electrodes and fluid circuits addressing each electrode individually. Also, the device may comprise an addressable array of electrodes and fluid circuits addressing the array collectively. That is, the fluid circuits do not have to be designed to deliver separate reagents to each electrode. The same mixture (e.g. dNTPs) can be delivered to each electrode with a target molecule attached. A semiconductor substrate is provided with integrated circuits for connections to electrodes and for the amplifying circuits and channels for the fluid circuits. Microfluidics may be used, and the channels for delivering reactants may comprise a polymer, e.g. poly (dimethylsiloxane) (PDMS) and/or Poly (silarylene siloxane) (PSS).

The present invention further includes methods for fabricating such a device, and methods for using such a device.

DETAILED DESCRIPTION OF THE PREFERRED EMBODIMENT

Introduction

Figure 1:
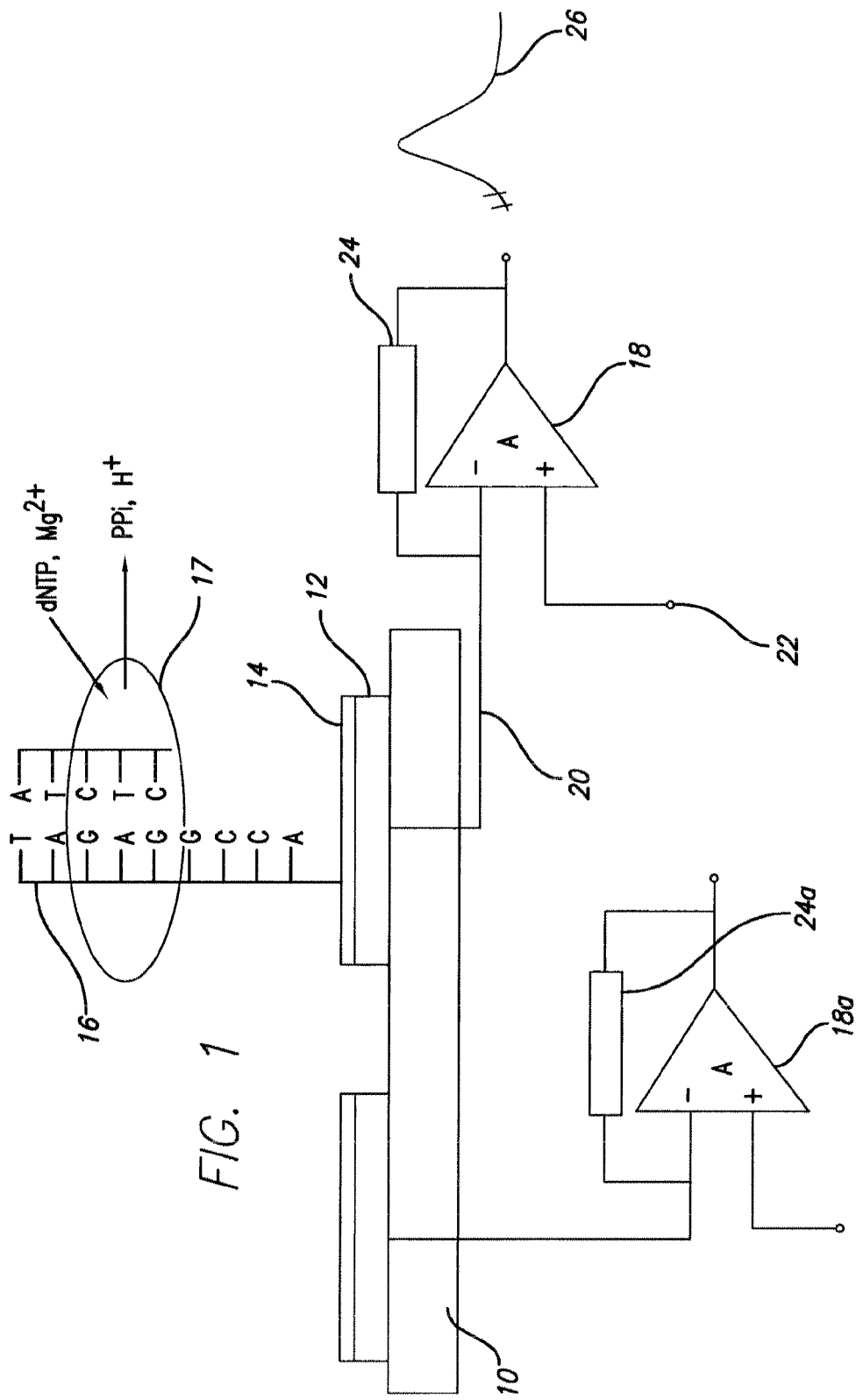
FIG. 1 is schematic diagram of a charge perturbation detection system.

The present device allows for direct detection of electric charge perturbations of the local environment by an electrode system. When used with immobilized DNA, it can uniquely identify a DNA sequence. The polymerization process generates local perturbations of charge in the solution near the electrode surface and induces a charge in the polarizible electrode. This event is detected as a transient current by a voltage clamp amplifier. Detection of single nucleotides in a sequence can be determined by dispensing individual dNTPs to the electrode solution and detecting the charge perturbations. Alternatively, multiple bases can be determined at the same time using a mix of all dNTPs with subsequent analysis of the resulting signal. The initial enzyme attachment to the DNA molecule can be detected prior to polymerization with a surface electrode capacitance measurement using the same voltage-clamp amplifier. This technique thus enables also the detection of enzyme-DNA interactions at the electrode surface.

Based on current understanding of polarizable interfaces, and without wishing to be bound by any particular scientific theory, it is believed that the electrode is polarized, i.e. has a potential difference between the exposed surface and the electrode, so that the negative charge appearing in excess at the gold electrode surface is inducing the charge of equal amount, but opposite in sign, on the other side of the interphase without crossing the interfacial region. A negative induced charge on the side of the electrode, which is not facing the solution would be detected and amplified by a voltage clamp amplifier. According to principles of electricity and magnetism, a charged object located in the vicinity of a conducting surface will cause electrons to move in the surface material even though there is no physical contact. This is illustrated in a simple electroscope, where a charged item held near foils causes them to separate. In this case, the charged item would be the target molecule (DNA) and the electrode would become charged and fed into the voltage clamp amplifier.

It is therefore possible to detect DNA sequences of target molecules by the present Charge Perturbation Detection system by measuring characteristic transient current events by a voltage clamp amplifier. Signal or pattern recognition analysis of these events can be used to determine the sequence of target molecules or identifies the target molecule itself.

Four different principal methods used by this technique are:
(1) Detection of the transient current events of the DNA polymerization by adding individual dNTPs.
(2) Detection of the transient current events of the DNA run-off polymerization by adding a mix of all dNTPs to electrode solution.
(3) Detection of the enzyme interactions (e.g. attachment) with DNA molecule by measurement of capacitance changes of the electrode interface.
(4) Detection of a multiple DNA molecules and their mutations by multi-electrode Charge Perturbation System.

A further aspect of this invention is the use of electrode coating with various layers to enable detection of DNA sequence by Charge Perturbation Detection system. The coating also enables and creates conditions for tethering a probe/template molecule to the electrode surface.

The use of a template is designed to allow specificity of the reaction, as according to well-known rules of base pairing (Watson Crick pairing), A binds to T or U and G binds to C. The rapid and sensitive detection of nucleic acids in a sample can provide a point-of-care diagnostic device that can test a patient's sample for the presence of specific known pathogens and determine the proper course of treatment. This can also be useful for current research applications that use DNA microarrays for readout. Instead of labeling test samples with fluorescent molecules and hybridizing the DNA to microarrays, the samples can be hybridized to electrode surface and detected with this system. This would result in faster and more accurate quantitative data with multiple sequence detection in one test.

Charge Perturbation Detection of DNA Sequence Polymerization Concept: Introduction and Overview The device described in detail below demonstrate that the electrical signal created by polymerization of nucleic acids, and other biochemical reactions is detectable and can be easily acquired using commercial electronic components. Without extensive optimization, the sensitivity of the prototype was superior to that of commonly used optical detection systems such as real-time PCR systems.

CPD (Charge Perturbation Detection) technology does not require modified nucleotides or marker molecules to detect polymerization signals. Through application of sensors that are implemented in CMOS technology, individual polymerization steps can be detected in real time and easily processed. Not only does CPD avoid costly labels and specialized readout equipment, but as noted above, preliminary results suggest that CPD is also more sensitive. Because target DNA can be detected at concentrations below 10 fmol, the present system does not need amplification of target DNA. Experimental systems have been fabricated that can detect 1-10 femtomoles ($1$-$10\times10^{-15}$ moles) of DNA, an order of magnitude higher detection sensitivity than commercial pyrosequencing or single-base extension technologies.

The underlying principle of CPD is the detection of the transient current that is generated by the immobilization of charged molecules onto a measurement electrode. In the case of DNA detection, transient current is generated by proton removal as a complementary deoxynucleotide-triphosphate (dNTP), incorporated into a nascent strand on the measurement electrode (upon which the target is immobilized with a probe that acts as a primer), and accompanied by proton removal during biomolecular reaction. The current signal is detected by the measurement electrode. A characteristic current waveform is generated that can be interpreted in terms of the polymerization rate of the participating dNTP molecules. The resulting electrical signal is transient and is not present once the polymerization reaction is complete (i.e., over time, the rate of change in net charge becomes zero).

Figure 3:
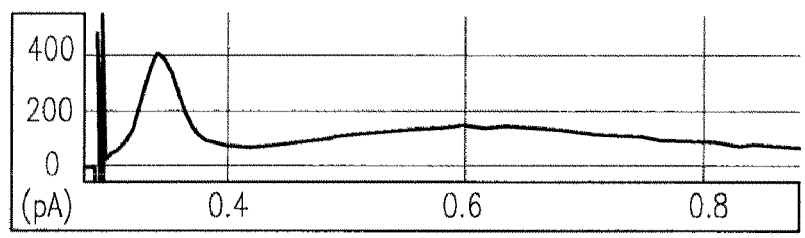
FIG. 3 is a current trace of addition of a complementary nucleotide (3A); noncomplementary nucleotide (3B); and multiple nucleotides (3C)
Figure 3:
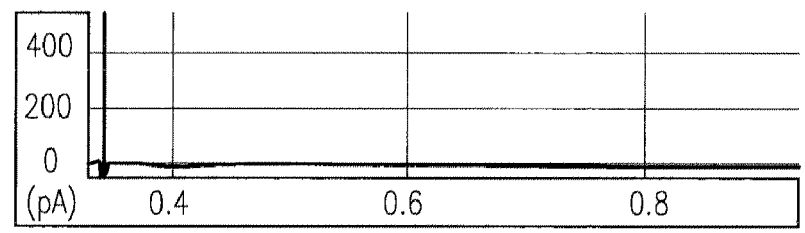
Figure 3:
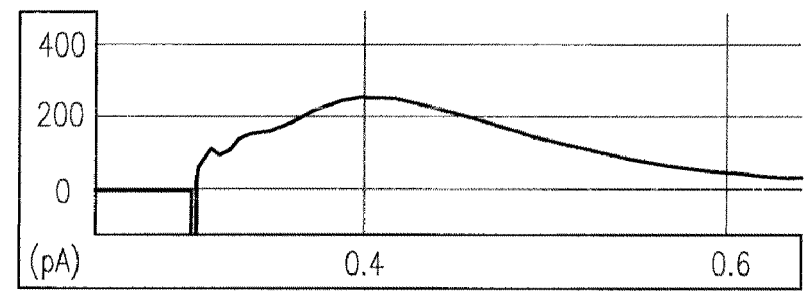

CPD differs from traditional electrochemical measurement techniques where the applied potential difference speeds up the rate of oxidation or reduction in order to sense the rate of diffusion of a reactant in the vicinity of the electrode surface. Our sensor applies a constant zero potential to the measurement electrode through a feedback loop to compensate for accumulated charge at the electrode surface and to prevent diffusion of equilibrating counter-ions. The CPD detection method actively senses transient current that results from changes in the electrical charge during chemical reactions in the solution. The chemical reactions that are detected are near, but not at the electrode/solution interface, and no charge flows through the interface. Using the example of the incorporation of dNTPs, the signal is subsequently converted into a current signal by a high-gain voltage-clamp amplifier. Upon sequential additions and washouts of individual dNTPs, nucleotide sequence peaks will appear as is shown in a sequence polygram (FIG. 3). This simple procedure will identify an unknown sequence in the immobilized template strand.

The detection mechanism of the CPD devices are based on the charge conservation principle, where the increase of the total negative charge on the DNA molecules is exactly compensated by an increase of the total positive charge in the solution resulting from an increase of proton concentration. Each of these electrical charges induces a surface charge, opposite in sign, on the coated, electrically isolated but highly polarizable, gold electrode. The magnitude of any induced charge is a function of the electrode surface geometry and the distance between the electrode and the inducing charge. For electrodes used in these experiments, the magnitude of the induced charge is effectively constant for separation distances in the range of ~1 nm up to ~30 µm (the detection zone), and steeply decreases for distances >30 µm (FIG. 5B). The charges on a DNA molecule attached to the electrode are locally fixed in close proximity to the electrode surface (<100 nm). The protons released from DNA are free to rapidly diffuse in the solution far enough to produce a change of the net charge in the detection zone. This event induces a charge sensed by the polarizable electrode. Since the electrode is held at a constant potential, the charge induced by an individual molecule results in a small pulse of current in the electrode. The sum of these current pulses from all DNA molecules attached to the electrode surface produces a large transient current detected by the voltage-clamp amplifier. Ideally, the measured current is equal to the time rate of change in net charge within the detection zone during the reaction, expressed by the equation $I(t)=dQ(t)/dt$ (where Q is charge, I is current and t is time). To evaluate actual efficiency of signal transduction, surface DNA density was measured by polymerization of radiolabeled dCTP. This showed that approximately 1 femtomole of DNA was immobilized on the electrode surface (0.0009 cm$^2$), which corresponds to ~$6.7\times10^{11}$ DNA molecules per cm$^2$ of the electrode. This result correlated well with the calculation of DNA surface density of ~$6.0\times10^{11}$ molecules per cm$^2$ based on the size of the electronic CPD signal of polymerization, indicating that the efficiency of signal transduction of the CPD electrode is very high.

As discussed below in connection with FIG. 2, an incoming dNTP molecule, complexed with one $Mg^{2+}$ ion (Ref. 15), increases the negative charge by $2e^-$. Incorporation of the catalytic $Mg^{2+}$ ion (Ref. 16) decreases the negative charge by $2e^-$. Incorporation of a complementary nucleotide then increases a negative charge by $1e^-$ on the new backbone phosphate group, produced by removal of a proton from the 3'-OH group of the DNA primer during the catalytic step of the reaction (Ref. 17), followed by rapid diffusion of the proton into the surrounding solution. The change in the induced charge can be detected by the electrode as a transient current measured by a voltage-clamp amplifier. The diffusion distance of low-molecular-weight compounds ($Mg^{2+}$, $MgdNTP^{2-}$, $MgPi^{2-}$) in solution during the time course of the experiment (1 s) is approximately an order of magnitude slower than proton diffusion. For this reason the charge changes induced by most of the reaction steps (binding of the dNTP molecule, complexed with one $Mg^{2+}$ ion, incorporation of the catalytic $Mg^{2+}$ ion, dissociation of the catalytic $Mg^{2+}$ ion and of the leaving $Mg^{2+}$-bound pyrophosphate) do not produce a measurable electrode response. On the same basis, the Brownian motion of ions in the solution as well as conformational changes of the immobilized enzyme and DNA molecules do not produce changes in the induced charge.

In one embodiment, a prefabricated electrode matrix was used for DNA immobilization. The electrically active 1×2 cm Au chips (shown in FIGS. 1 and 4) were manufactured using a semiconductor-processing technique on a 4-inch wafer at the Stanford Nanofabrication Facility (SNF). The chips consisted of four pairs of rectangular gold electrodes that were 0.09 mm$^2$ with 0.5 mm center-to-center spacing. For measurements of electrical activity of the CPD electrode an Axopatch 200B voltage-clamp amplifier (Axon Instruments, Union City, Calif.) was used. The Axopatch amplifier was used in the whole-cell voltage-clamp mode with the holding potential at 0 mV. The high-impedance coating of the CPD measurement electrode prevents the occurrence of faradaic current that could otherwise cause interference or the deterioration of the sensor and analytes. A reference Ag/AgCl electrode of the voltage-clamp amplifier was immersed directly in the bathing solution during measurements.

For the initial experiments, single-stranded DNA molecules (76 bases) with different sequences were chemically synthesized with a thiol modification on the 5'-terminus and HPLC purified by MWG Biotech (High points, NC, USA). The DNA sequences were designed to self-prime with a 19 base-pair self-complementary sequence at the 5'-end of the DNA. Approximately 40 bases of the DNA sequence are single stranded and extendable by DNA polymerase.

Self-priming, single-stranded DNA molecules were immobilized on the surface of a gold electrode through a thiol-reactive self-assembled monolayer (SAM). The electrode was equilibrated with 10 units of the Klenow (exo) fragment (KF) of DNA polymerase. FIG. 3A shows the signal resulting from the addition of a solution containing a single dNTP (1 mM concentration in final solution volume) complementary to the nucleotide in the template sequence (top black trace).

The dNTPs used in the present system do not require any type of labeling, nor is any reporter molecule used in the present system. This prevents problems associated with different incorporation parameters for labeled dNTPs. Readouts of sequences of various lengths are thus possible.

With no measurable delay, current rises to a peak of ~400 picoamps (pA) within ~50 milliseconds (ms), rapidly decreases to ~50 pA, and then shows a further, slower transient increase to ~150 pA within 300 ms. The current transient is almost completed at 1 second (<5% of peak current). The integral of the measured current is 87 picocoulombs (pA·s), corresponding to nucleotide incorporation to ~$6.0 \times 10^{11}$ DNA molecules per $cm^2$ of the electrode. In contrast, if a solution containing a non-complementary dNTP was added, no current transient was observed (FIG. 3B). No signal was produced when the complementary dNTP was added in the absence of DNA polymerase, in the absence of DNA, or if DNA was not immobilized on the electrode surface. The lack of detectable signal in the control experiments demonstrates the clear dependence of the current transient on the complementarity of the actual nucleotide, and on the simultaneous presence of KF (Klenow fragment) and immobilized DNA. The current waveform observed can therefore be attributed to the signal resulting from the incorporation of the nucleotide into the primer strand.

Fabrication of Gold Chips

Electrically active 1×2 cm Au chips were manufactured using a semiconductor processing technique on a 4-inch wafer at the Stanford Nanofabrication Facility (SNF) (http://snf.stanford.edu). The pairs of electrodes on the Au chips were arranged so that each electrode pair was orthogonal to the adjacent pair, forming a generally square pattern of electrodes. Eight parallel leads were formed, extending from each electrode to the edge of the chip. The process requires only a single mask, designed on an industry-standard CAD program and produced on a piece of Mylar thin-film. A 500 µm-thick quartz layer is used as the substrate. The process flow is as follows: A very thin layer of chromium is first deposited to improve the adhesion between gold and quartz. Next, a 1000 Å thick gold layer is deposited to define the pattern for both the electrodes and the connecting pads. The minimum feature size of this chip is 200 µm. To prevent contamination after processing, a 7-µm-thick photoresist is used as a protection layer. After dicing, the photoresist is washed off with acetone and isopropanol. The chips consisted of four pairs of rectangular gold electrodes that were 0.09 $mm^2$ with 0.5 mm center-to-center spacing. Other areas on the chip were used for the connection pads to external devices.

Surface Modification

All reagents used for surface modification were of reagent grade and used as received from Aldrich unless otherwise stated. The patterned quartz chips were cleaned in an RCA cleaning solution ($H_2O$: $NH_4OH$: 30% $H_2O_2$, 5:1:1, v/v/v) for 15 min at 70° C., immersed in a water bath for 10 min and dried in a stream of argon. The quartz surface was coated with a hydrophobic octadecyltriethoxysilane (Gelest, Morrisville, Pa.) in an anhydrous toluene solution containing 1% (v) silane and 2% (v) hexanoic acid for 24 hr at room temperature. Silanized chips were washed twice with toluene and once with ethanol for 5 min each, and dried in a stream of argon. The silanization step was performed to make the quartz surface hydrophobic and thereby avoid cross contamination between gold electrodes in close proximity to each other during spotting.

The gold electrodes were coated with a long-chain thiol to form a densely packed monolayer (a self-assembled monolayer [SAM]), which displaces any physisorbed silanes (Refs. 25, 26), i.e. silanes physically absorbed on the surface. The silane-coated chips were immediately immersed in a 1 mM solution of mercaptoundecanol (MUD) in ethanol for at least 16 hr. The gold substrates were removed from the thiol solution, washed with ethanol, and dried under an argon stream. The hydroxyl-terminated monolayer was transformed into a thiol-reactive moiety by exposure to a 2.3 mM solution of N-(p-maleimidophenyl) isocyanates (PMPI, Pierce, Rockford Ill.) in anhydrous toluene at 40° C. for 2 hr under an argon atmosphere. (Refs. 27,28)

Suitable long chain thiols for linking to the electrode surface and the test molecule (DNA strand) are generally between about 3 to 24 carbon long. Generally, the electrode has bound to it an SAM linked to the electrode at a thiol group at one end; a long chain alkyl group, and a linker group for attachment to a nucleic acid (DNA) at the other end. A suitable linker group is PMPI.

Other suitable SAMs are described in U.S. Pat. No. 6,652,398, hereby incorporated by reference for purposes of describing SAMs containing phytanylthiol. As described in U.S. Pat. No. 6,048,623 to Everhart, et al., issued Apr. 11, 2000, entitled "Method of contact printing on gold coated films," incorporated by reference for further description of suitable SAMs, the self-assembling monolayer may have the following general formula:

X—R—Y where X reacts with the metal (gold) electrode, R is a linear or branched alkyl or polymer backbone; and Y reacts with a nucleic acid, e.g. a thiol functionalized DNA. The DNA linkage may be through a phosphate to a sulfur group on a PMPI linker. The PMPI linker is attached to the SAM and to the DNA. PMPI (N-[p-Maleimidophenyl]isocyanate) is useful because both hydroxyl and sulfhydryl reactivity can be found in this cross-linker. Maleimide reacts with —SH groups at pH 6.5-7.5, forming stable thioether linkages. Isocyanate reacts with —OH groups to form a carbamate link at pH 8.5. It is an excellent tool for conjugating —OH group-containing compounds.

X is designed to be reactive with metal or metal oxide. For example, X may be asymmetrical or symmetrical disulfide (—R'SSR, —RSSR), sulfide (—R'SR, —RSR), diselenide (—R'Se—SeR), selenide (—R'SeR, —RSeR), thiol (—SH), NH2, nitrile (—CN), isonitrile, nitro (—NO.sub.2), selenol (—SeH), trivalent phosphorous compounds, isothiocyanate, xanthate, thiocarbamate, phosphine, thioacid or dithioacid, carboxylic acids, hydroxylic acids, and hydroxamic acids.

Maleimide-modified gold electrodes were washed with anhydrous toluene and dried in a stream of argon. The various surface modification steps were followed by X-ray photo-electron spectroscopy (data not shown) and the presence of the expected elements and peak shifts confirmed the proper transformation of both surface components.

An SAM may also be formed of polymers that bind to gold and or other electrode materials. For example, Major, et al. "Strategies for Covalent Multilayer Growth," Chem. Mater. 2002, 14, 2574-2581 describes a strategy for the covalent assembly of polymer multilayers at interfaces, where growth is accomplished one layer at a time. The individual layer constituents are maleimidevinyl ether alternating copolymers with side groups that possess reactive functionalities. The identity of the polymer layer side groups determines the chemistry employed in interlayer linkage formation. It is reported there that one may carry out the selective creation of amide, ester, ether, urea, and urethane interlayer linkages.

The SAM serves to provide insulation for the electrode and to prevent non-specific adhesion of DNA to the electrode. The SAM facilitates the orientation of the DNA in a parallel linkage to the substrate.

Immobilization of DNA

The thiolated oligonucleotides were diluted to a final concentration of 10 μM in 0.1M phosphate buffer, pH 7.4, with 10 μM dithiothreitol (DTT) and incubated at least 1 hour at room temperature. Immobilization of the reduced thiolated oligonucleotides onto the electrodes was performed manually by deposition of 0.2 μl reduced oligonucleotides followed by overnight incubation at room temperature in a humidified chamber.

Design, Synthesis and Purification of Oligonucleotides

Single-stranded DNA molecules (76 bases) with different sequences were chemically synthesized with a thiol modification on the 5'-terminus and HPLC purified by MWG Biotech (High points, NC, USA). The DNA sequences were designed to self-prime with a 19 base-pair self-complementary sequence at the 5'-end of the DNA. Approximately 40 bases of the DNA sequence are single stranded and extendable by DNA polymerase. The oligonucleotide used in the experiment (FIG. 1) was:

```
                                              (SEQ ID No: 1)
5'-Thiol/TTTTTTTTTTTTTTTTTTTGCTGGAATTCGTCAGTGACG

CCGTCGTTTTACAACGGAACGG CAGCAAAATGTTGC.
```

Prototype Sensor System

In a typical charge-based sensor system, a prefabricated electrode matrix is used for DNA immobilization. The electrodes were fabricated as described above. The CPD electrode chip that was used in these experiments is further described in the section "fabrication of gold chips.". The electrode surface was submersed in a standard DNA polymerization buffer (5 mM Tris-HCl, pH 8.3; 25 mM KCl and 1.25 mM $MgCl_2$) with DNA polymerase (10 U, Klenow fragment). Polymerization was initiated by adding a 2 μl aliquot containing 20 mM of dNTP substrate (to give 1 mM final concentration of dNTP in 40 μl buffer).

Electrical Measurement Method

For measurements of electrical activity of the CPD electrode was used an Axopatch 200B voltage-clamp amplifier (Axon Instruments, Union City, Calif.). The Axopatch amplifier was used in the whole-cell voltage clamp mode with the holding potential at 0 mV. The high-impedance coating of the CPD measurement electrode prevents the occurrence of faradaic current that could otherwise cause interference or the deterioration of the sensor and analytes. A reference Ag/AgCl electrode of the voltage-clamp amplifier was immersed directly in the bathing solution during measurements.

Other Amplifier Designs

A voltage clamp amplifier may described generically as a differential feedback amplifier having one input at a fixed voltage outside the container and another input attached to the electrode. Many general-purpose op amp chips have two or four separate operational amplifiers in one package, with common power supply connections. In practice the ideal amplifier criteria requirements are met only approximately, but as will be shown, close enough for most purposes. Practically, an op amp will have a gain of 10,000 or more, an input impedance of megohms, and a 3 dB bandwidth of several tens of hertz or more. If an amplifier has a 3 dB bandwidth of 40 Hz and a gain of 100,000 times, this is a gain bandwidth product of 4 million hertz, or 4 MHz (40×100,000). It is advantageous in many feedback applications to have the gain falling at 6 dB per octave or 20 dB per decade at frequencies beyond the corner frequency (that frequency at which the amplifier gain has fallen 3 dB or 70.7 percent of its DC value). Since the op amp is used in mainly in feedback circuits having much lower closed loop gain, these performance figures are good enough in many cases. In fact, even a single high gain (100×) common emitter transistor amplifier stage can be treated as an op amp if feedback is employed, with surprisingly little error. In many cases a single transistor will work almost as well as a more expensive op amp device. One example is a simple audio amplifier stage from which a moderate gain (5-20×) is required.

Radiolabeling

Radioactive labeling and phosphor imaging techniques were used as process controls to quantify the oligonucleotide attachment and subsequent hybridization reactions.29 [a-32P] dCTP (Pharmacia) was used for 3' labeling of the attached self-primed probes via single-base extension. Specific activities of the radiolabeled oligos were determined by liquid scintillation counting using an LS 7500 liquid scintillation system (Beckman Inc., Columbia, Md.). Standard curves were made from a serial dilution of known amounts of the 32P-labeled nucleotides used in the experiments. The data presented here represent the averages of, minimally, three replicate points.

Example 1

(FIG. 1): Schematic Diagram of Charge Perturbation Detection System

FIG. 1 is a schematic diagram of a device according to the present invention, with attached enzyme and substrate, showing the generation of ions and the detection circuitry. The device is formed on a substrate 10, by the attachment of a metal electrode 12, preferably of an oxidation resistant, high potential metal such as gold. A coating or insulation layer 14, may also be applied to the electrode 12. A template DNA strand 16 is attached to the electrode structure. A primer DNA strand is hybridized to the template DNA strand 16. Deoxynucleotide triphosphate (dNTP) and $Mg^{2+}$ ions are added. Incorporation of the complementary dNTP releases inorganic pyro phosphate (PPi) and $H^+$ ions (protons). A DNA polymerase complex is illustrated at 17 and ion movement is shown relative to the enzymatic reactions, i.e. dNTP, $MG^{2+}$ in and PPi and $H^+$ out.

As described below, the charge perturbation in the vicinity of the electrode is detected by a voltage clamp amplifier 18 having a negative lead 20 connected to the electrode 12 and a positive lead connected to a command voltage source 22. Feedback resistor 24 serves to eliminate current output whenever the command voltage is equal to the reference voltage at the measurement electrode. When a small charge perturbation occurs at the electrode 12, an amplified, transient signal 26 is produced. A reference electrode, which does not have a template DNA strand attached to the electrode structure can be also provided (but is not required). The reference electrode is connected to a similar op amp 18a with feedback resistor 24a to provide a reference signal for comparison against the transient signals from the reaction electrode.

Prior to the start of the polymerization reactions, a DNA template is immobilized on a coated electrode surface. DNA polymerization requires the hybridization of a sequencing primer to this strand, so that DNA polymerization with attached enzyme can proceed with dNTP dispensations to the electrode solution and the sequence of the template strand can be detected. The system can also be designed to detect the hybridization of a template strand that is specific for a sample to be analyzed, in which case the sequence of the template strand is already known and the reaction detects the presence of a complementary primer strand in the sample to be analyzed.

Example 2

(FIG. 2): Template Orientation and Operation

DNA polymerase catalyzes the incorporation of complementary nucleotides, resulting in perturbations of local electrical charge. Perturbations are based on interactions of system components and release of products of polymerization. These local perturbations of charge in solution induce a charge in coated polarazible gold Charge Perturbation Detection system (CPD) electrode. This event is detected as a transient current by voltage clamp amplifier, which compensates induced charge in the gold electrode. The high-impedance coating prevents faradaic current that could deteriorate the sensor and analytes. For measurements of electrical activity of CPD electrode was used Axopatch 200B voltage clamp amplifier, but in principle any voltage-clamp amplifier can be used. Voltage command was kept at steady 0 mV holding potential, but because no faradaic current is present the voltage command can be kept on different holding potentials and can be used for various purposes in the final system. For example, a specific voltage can repel various polymerization products or ions and "clean" the surface of the electrode for next polymerization steps.

Figure 2:
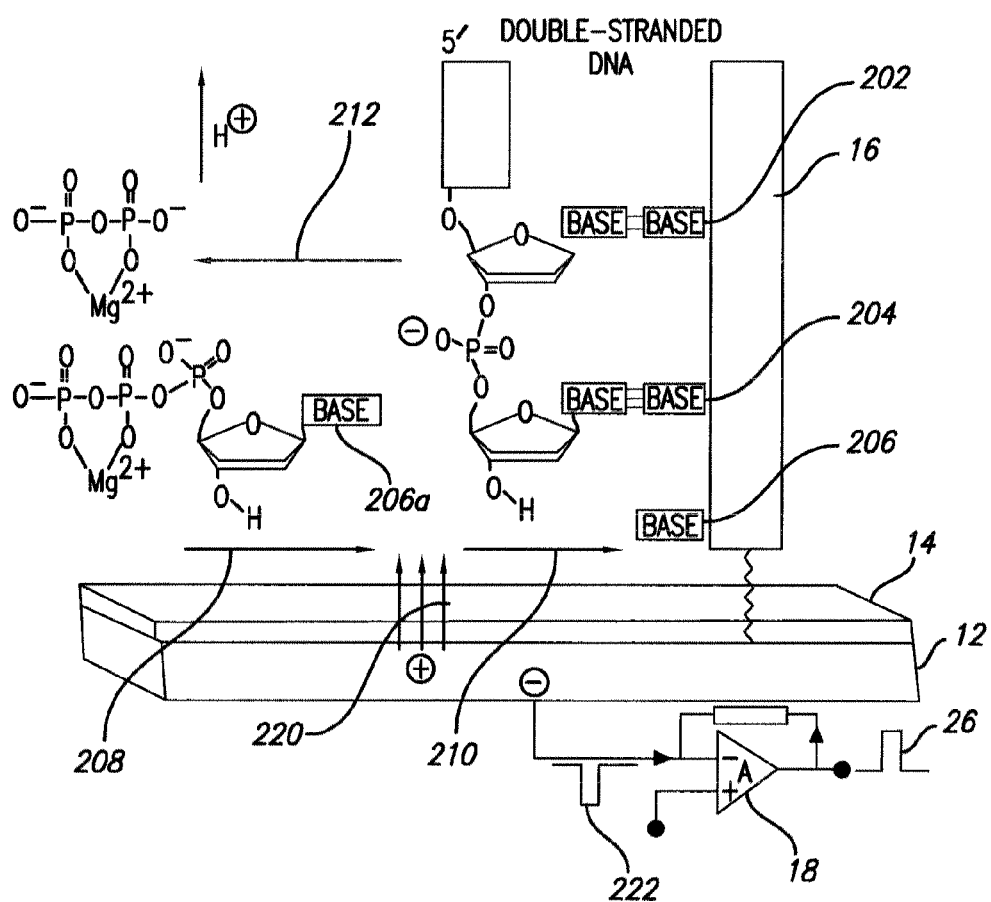
FIG. 2 is a schematic showing the device of FIG. 1 as it operates in a DNA polymerization reaction.

FIG. 2 shows base pairing that has already occurred at positions 202 and 204. Template strand base 206 is about to be paired with a base 206a, which includes triphosphate. Two of the phosphates are stabilized with a magnesium ion, as is known to be required by DNA polymerase. Arrow 208 shows the dNTP with base 206a prior to incorporation; arrow 210 represents incorporation of base 206a. Base 206a is then linked to the growing (primer) strand through the phosphate backbone. At that point, there is a new charge incorporated into the primer strand phosphate backbone, and, as shown by arrow 212, there is liberated $H^+$, PPi (inorganic pyro phosphate) and catalytic $Mg^{2+}$. The $H^+$ diffuses away and an electron is repelled from the electrode 12 interfacing solution, causing a positive induced charge in the electrode, as shown by arrow 220, and a negative current pulse 222 that is detected by the sensitive amplifier 18. The sensitivity is provided by a voltage clamp circuit and amplified to an output signal 26.

Capacitance Measurement

Measurement of the electrode capacitance is used to detect attachment of an enzyme to the DNA located at the surface of the electrode. This step will easily eliminate problematic electrodes and speed up measurement of electrodes with correct enzyme/DNA interaction. Capacitance increase of electrode interface is probably caused by the change of DNA dielectric layer due to the enzyme attachment to the DNA. If there is a problem of enzyme/DNA attachment or in the electrode surface chemistry fabrication (e.g. thickness of coated layers) then no significant increase in capacitance is observed even all components are present in the solution. Increase of capacitance in current version of electrodes (size, layers, enzyme, buffer concentration, DNA density) is about 5-6 fold and can depend on mentioned parameters. Without wishing to be bound by one theory as to the cause of this effect, it is thought that target molecules (DNA strands) with attached enzyme "stand up," i.e. are aligned away from the electrode, allowing solution to be closer to the SAM, effectively making the dielectric thinner.

Measurement of capacitance is based on applying small (e.g. ±2 mV) triangle-wave voltage command to the electrode and detecting response square-wave current recalculated to capacitance by equation: $C=I/(dV/dt)$. Measurement of electrode capacitance enables also detection of general interactions of enzymes with the target molecule (DNA) located at the surface of the electrode.

Example 3

(FIG. 3): Analysis of Signals

If the addition of individual dNTPs is performed sequentially, then nucleotide sequence peaks will appear as shown in a sequence poly-gram (FIG. 3). The individual detected signal is shown in FIG. 3A and FIG. 3C. If the addition of dNTPs is performed with a mix of all nucleotides then a run-off polymerization signal is detected (FIG. 3C). This signal can be then analyzed and multiple nucleotide bases can be determined by the shape of the curve, which will vary in response to the particular nucleotide incorporated.

In FIG. 3A, the addition of a dGTP binding to a C nucleotide in the template is shown. The spikes at the beginning of the signal are caused by dispensation disturbance and initial diffusion of dGTP solution and are easily filtered out. With no measurable delay after dispensation, current rises to a peak of ~400 picoamps (pA) within ~50 milliseconds (ms), rapidly decreases to ~50 pA, and then shows a further, slower transient increase to ~150 pA within 300 ms. The trace in FIG. 3B shows that no signal is generated in the absence of a reaction near the electrode interface.

Example 4

(FIG. 4): Electrode Fabrication and Chemistry

Figure 4:
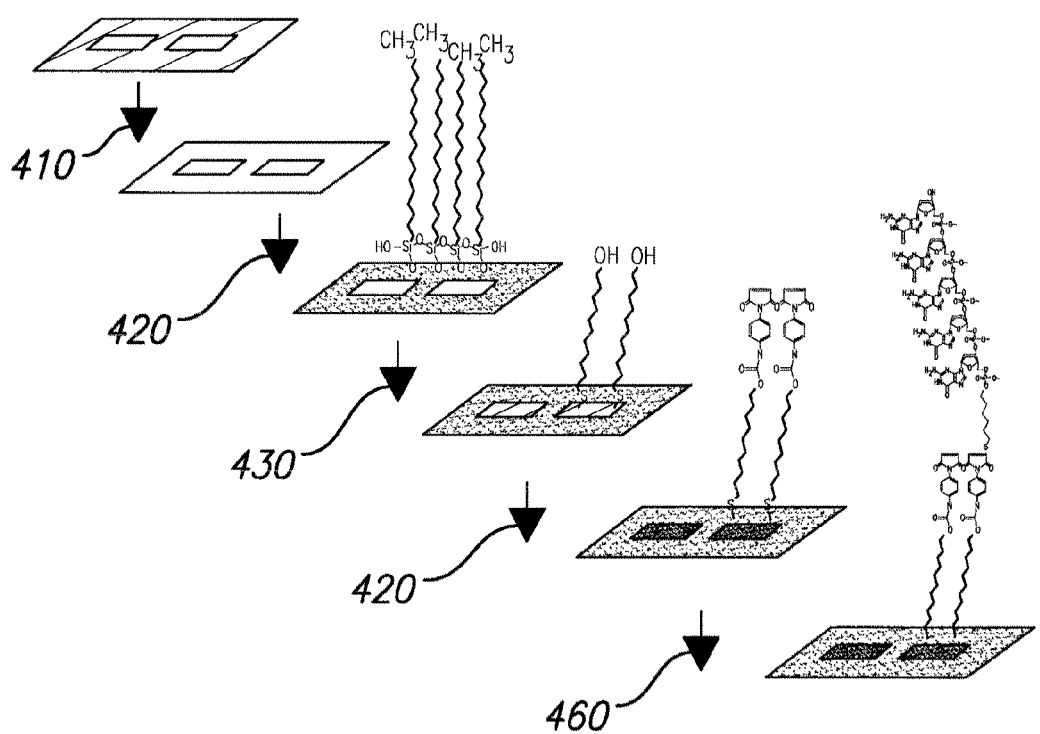
FIG. 4 is a schematic drawing showing fabrication and surface chemistry of a preferred embodiment of the present invention.

Fabrication of a "CPD chip" (Charge perturbation detection chip) on a glass wafer is illustrated in FIG. 4, in which the steps in a surface chemistry process to produce coated electrodes with immobilized DNA are outlined. The size of the illustrated electrode is 0.3×0.3 $mm^2$ and the distance between two electrodes in each electrode pair is 0.2 mm. Most part of the chip excluding the electrodes and a part of the paths is covered by a dielectric layer (silicon oxide) to avoid direct contact between the paths and the solution. The number of electrodes is not limited by the design and it will vary in individual applications, number of sequences to be detected and/or micro fluidics to be used. The electrodes described in FIG. 4 are manufactured using semiconductor-processing technique on a 4-inch wafer (FIG. 4) at the Stanford Nanofabrication Facility (SNF). The process requires only a single mask that is designed using an industry-standard CAD program and produced on a piece of mylar thin-film. A 500 µm thick quartz layer is used as the substrate. The process flow works as follows: A very thin layer of chromium is first deposited to improve the adhesion between gold and quartz. Next, a 1000 Å thick gold layer is deposited to define the pattern for both the electrodes and the connecting pads. The minimum feature size of this chip is 40 µm. To prevent contamination after processing, a 7 um thick photoresist is used as a passivation layer.

In step 410, the gold electrode is cleaned with a standard cleaning process:

1) UV Ozone cleaner, from Jelight Company Inc. (www.jelight.com)
2) Plasma oven from 4th state inc (www.4thstate.com)
3) RCA cleaning, containing water, ammonium hydroxide, hydrogen peroxide (5:1:1).

In step 420, a silane layer is applied to areas surrounding the electrode. In step 430, a self-assembled monolayer is attached to the electrode areas where the DNA template will be immobilized. Next in situ formation is carried out in step 440. This creates a reactive group for the attachment of a sulfur-containing DNA strand in step 460. That is, after attaching the monolayer 442 linked to the gold, a layer of PM-I-N-(pMaleimidophenyl) isocynate 444 is used to attach covalently thiol modified DNA 462 to the PMPI.

CPD electrodes coated as described above may be placed into a holder in order to contain the chip and provide fluid paths and electrical connections. Electrode output is connected to the Axopatch 200B amplifier or equivalent voltage-clamp device (Axon Instruments, Foster City, Calif.). The sample solution (e.g. 40 µl), consisting of buffer (5 mM Tris-HCL, pH 8.3 (at 25° C.); 25 mM KCl and 1.5 mM $MgCl_2$) is dispensed into an electrode chamber.

Example 5

Operation of Illustrated Embodiment

Self-priming, single-stranded DNA molecules were immobilized on the surface of a gold electrode through a thiol-reactive self-assembled monolayer (SAM). The electrode was equilibrated with 10 units of the Klenow (exo-) fragment (KF) of DNA polymerase.

Initial capacitance of the electrode was measured by triangle-wave voltage, as described above under "Capacitance Measurement." A sawtooth waveform is applied to the command voltage. Then polymerase enzyme (e.g. 2 µl) is introduced to the solution. After several minutes, electrode capacitance is measured. Correct attachment of enzyme is confirmed by increase of electrode capacitance. The amount of increase depends from the size of electrode and DNA density and should be several times higher than initial capacitance without enzyme (e.g. 5x). Finally individual dNTPs, or a mixture of dNTPs, are rapidly dispensed in the solution. Speed of diffusion and dispensation should be in the range of several milliseconds in order to avoid disturbance of following polymerization reaction. Piezo-spray dispensation triggered by computer (piezo, RJ315 with Sone-Tek generator) was used for dispensation, but some other fast-perfusion system with for example air-pressure spritzer can be used as replacement (e.g. Spritzer-8 8-Channel Micro Injector—Spritzer from BioSciense Tools, Inc.). Concentration of dNTPs can be scaled according to signal sensitivity. Signal to noise ratio is based on size of the electrode, DNA density, solution concentration, etc.). We used for example 5 mM-20 mM sol of dNTP.

Transient ionic current is recorded using the Axopatch 200B amplifier in voltage-clamp mode with signal filtering at 5-10 kHz bandwidth. The signal is further digitized by an Axon Digidata 1320A digitizer with sampling frequencies from 10 kHz to 500 kHz. The data is recorded using Clampex 8 (Axon Instruments), and the same software is used for basic signal analysis.

The signal resulting from the addition of a solution containing a single dNTP (1 mM concentration in final solution volume) complementary to the nucleotide in the template sequence rises to a peak of about 400 picoamps (pA) within ~50 milliseconds (ms), rapidly decreases to ~50 pA, and then shows a further, slower transient increase to ~150 pA within 300 ms. The current transient is almost completed at 1 second (<5% of peak current). The integral of the measured current is 87 picocoulombs (pA·s), corresponding to nucleotide incorporation to ~$6.0 \times 10^{11}$ DNA molecules per $cm^2$ of the electrode. In contrast, if a solution containing a noncomplementary dNTP was added, no current transient was observed. No signal was produced when the complementary dNTP was added in the absence of DNA polymerase, in the absence of DNA, or if DNA was not immobilized on the electrode surface (data not shown; see priority provisional). The lack of detectable signal in the control experiments demonstrates the clear dependence of the current transient on the complementarity of the actual nucleotide, and on the simultaneous presence of Klenow fragment (KF) and immobilized DNA. The current waveform observed can therefore be attributed to the signal resulting from the incorporation of the nucleotide into the primer strand. The DNA polymerase-catalyzed elongation of the synthesized strand proceeds by the SN2 (bimolecular nucleophilic substitution) mechanism that has been extensively studied. (Refs. 9, 10, 11). Upon the incorporation of each nucleotide, the total negative electrical charge on the DNA molecule undergoes a net increase of $1e^-$, produced by the removal of a proton from the 3'-OH group of the DNA primer during the catalytic step of the reaction. (Ref. 12).

Example 6

(FIG. 5): Electrochemistry Reactions

Due to the principle of charge conservation, the increase of the total negative charge on the DNA molecules is exactly compensated by an increase of the total positive charge in the solution resulting from an increase of proton concentration. Each of these electrical charges induces a surface charge, opposite in sign, (Refs. 3, 4) on the coated, electrically isolated but highly polarizable, gold electrode. The magnitude of any induced charge is a function of the electrode surface geometry and the distance between the electrode and the inducing charge. For electrodes used in these experiments, the magnitude of the induced charge is effectively constant for separation distances in the range of ~1 nm up to ~30 µm (the detection zone), and steeply decreases for distances >30 µm (FIG. 5B). (Refs. 3, 4)

FIG. 5B shows the relative induced charge ($Q_{ind}/Q$) for the electrode surface geometry (x=0.3 mm, y=0.3 mm) as a function of the distance h between the electrode and the charge Q in the solution (Ref. 4). In the range of ~1 nm-~30 μm, the electrode response does not depend on the distance between the electrode and the ion. Therefore, the changes in the immobilized charge can produce a change of the induced charge on the electrode only if the released countercharge diffuses to a distance of >30 μm from the electrode surface, for the present size electrode.

The charges on the DNA molecule attached to the electrode are locally fixed in close proximity to the electrode surface (<100 nm), while the protons released from DNA are free to diffuse in the solution. For the duration of the experiment (~1 s), the diffusion distance of protons is >136 μm (the diffusion coefficient of proton $D_{H}^+$ in water is $9.3 \times 10^{-5}$ cm$^2$/s) (Ref. 13). Lateral proton diffusion might be significantly faster due to specific surface hydration of the electrode and the surrounding silane layer. (Refs. 14,15) The protons are thus able to diffuse far enough to produce a change of the net charge in the detection zone due to the immobilized negative charge on the DNA backbone. This event induces a charge sensed by the polarizable electrode. Since the electrode is held at a constant potential, the charge induced by an individual molecule results in a small pulse of current in the electrode. The sum of these current pulses from all DNA molecules attached to the electrode surface produces a large transient current detected by the voltage-clamp amplifier. Ideally, the measured current is equal to the time rate of change in net charge within the detection zone during the reaction, expressed by the equation $I(t)=dQ(t)/dt$ (where Q is charge, I is current and t is time). To evaluate actual efficiency of signal transduction we measured surface DNA density by polymerization of radiolabeled dCTP, as discussed above, indicating that DNA polymerization with as little as 1 fmole of DNA on a single electrode could be detected. Less than 1 fmole of DNA could be used as a template if a smaller electrode were used. To gain further insight into the mechanisms underlying CPD during a single step of the KF-catalyzed reaction, the kinetics of the reaction were studied. (Refs. 11, 16, 17, 18, 19, 20, 21)

Figure 5A:
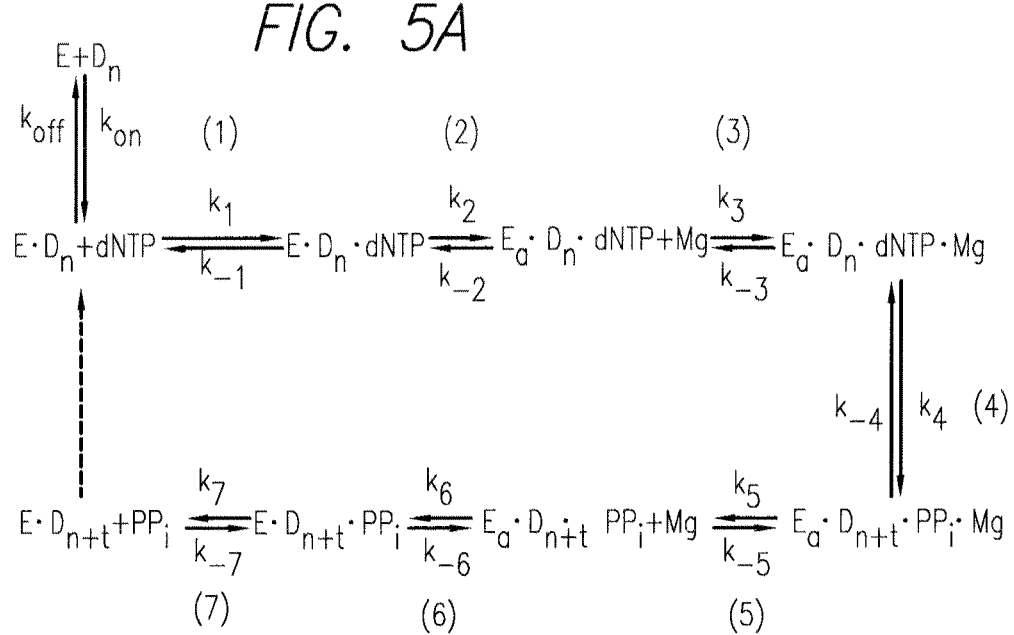
FIG. 5 is a scheme of kinetic mechanism of nucleotide incorporation by DNA polymerase (5A); a graph of the relative induced charge (Qind/Q) function for the electrode surface geometry (x=0.3 mm, y=0.3 mm) and source charge distance h (5B)
Figure 5B:
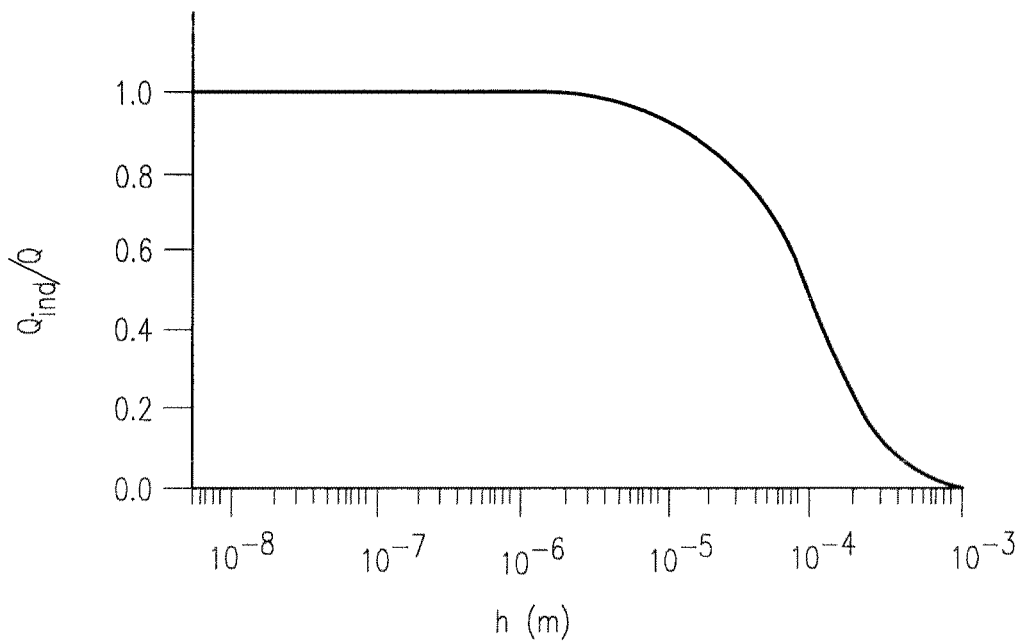

The kinetic scheme based on these studies is shown in FIG. 5A, which uses the following abbreviations: E: enzyme, Ea: active enzyme, Mg: magnesium, Dn: DNA with enzyme at n-th nucleotide, dNTP: deoxynucleoside 5'-triphosphate, PPi: pyrophosphate, kn: kinetic rate. The kinetic mechanism of nucleotide incorporation by DNA polymerase is shown initially to the left of arrows (1) (step 1). The enzyme forms initially a binary complex with the DNA primer-template (E·Dn). Upon addition of dNTP to the solution, the initial binding of an incoming complementary dNTP to polymerase produces a ternary substrate complex (step 1). After this step, the enzyme undergoes a subdomain motion to form a so-called closed or active state (step 2), which is followed by binding of the catalytic Mg$^{2+}$ ion (step 3) and by the chemical reaction of dNTP incorporation onto the DNA primer strand by the formation of a phosphodiester bond (step 4). Unbinding of the catalytic Mg$^{2+}$ ion (step 5) is followed by a second subdomain motion of the polymerase/product complex, resulting in an open state (step 6) followed by the release of pyrophosphate PPi (step 7) and subsequent DNA translocation.

Thus, the incoming dNTP molecule, complexed with one Mg$^{2+}$ ion, (Ref. 22) increases the negative charge by 2e$^-$. Incorporation of the catalytic Mg$^{2+}$ ion (Ref 23) decreases the negative charge by 2e$^-$ (1) Incorporation of nucleotide (2) then increases a negative charge by 1e$^-$ on the new backbone phosphate group (3), produced by removal of a proton from the 3'-OH group of the DNA primer during the catalytic step of the reaction (Ref. 12), followed by rapid diffusion of the proton into the surrounding solution (4). The change in the induced charge (5) can be detected by the electrode as a transient current (6) measured by a voltage-clamp amplifier (7). The diffusion distance of low-molecular-weight compounds (Mg$^{2+}$, MgdNTP$^{2-}$, MgPPi$^{2-}$) in solution during the time course of the experiment (1 s) is approximately an order of magnitude slower than proton diffusion (Ref. 24). For this reason the charge changes induced by most of the reaction steps (binding of the dNTP molecule, complexed with one Mg$^{2+}$ ion, incorporation of the catalytic Mg$^{2+}$ ion, dissociation of the catalytic Mg$^{2+}$ ion and of the leaving Mg$^{2+}$-bound pyrophosphate) do not produce a measurable electrode response. On the same basis, the Brownian motion of ions in the solution as well as conformational changes of the immobilized enzyme and DNA molecules does not produce changes in the induced charge.

Sample kinetic rates, using the notation of FIG. 5A, for a trace such as shown in FIG. 4A are as follows:
$k_{on}=1.2\times10^7$ M$^{-1}$s$^{-1}$,
$k_{off}=0.06$ s$^{-1}$, $k_1=1.25\times10^7$ M$^{-1}$s$^{-1}$,
$k_{-1}=250$ s$^{-1}$,
$k_2=50$ s$^{-1}$,
$k_{-2}=3$ s$^{-1}$,
$k_3=9.5\times10^5$ M$^{-1}$s$^{-1}$,
$k_{-3}=100$ s$^{-1}$,
$k_4=150$ s$^{-1}$,
$k_{-4}=40$ s$^{-1}$,
$k_5=100$ s$^{-1}$,
$k_{-5}=9.5\times10^5$ M$^{-1}$s$^{-1}$,
$k_6=4$ s$^{-1}$,
$k_{-6}=4$ s$^{-1}$,
$k_7=60$ s$^{-1}$,
$k_{-7}=1.45\times10^4$ M$^{-1}$ s$^{-1}$.

Based on this kinetic model, a simulation was performed to confirm whether this underlying mechanism accounts for the signal dynamics observed. The initial enzyme-DNA binding step was assumed to be in equilibrium during the simulation, since the enzyme was incubated for more than 2 minutes with the DNA attached to the electrode in the experiments. The published rate constants of individual reaction steps were used as the starting point of simulations, with the exception of step 3 and 5, for which we found no published KF rate constants. We approximated these steps with Kd~100 μM based on the published rate constants for DNA polymerase β (Ref. 19). We achieved a best fit between model and experimental signals by adjustment of selected kinetic rates (in particular, $k_6$, $k_{-6}$, $k_7$, $k_{-7}$ were changed somewhat from the previously published values to account for different experimental conditions) (Refs. 20, 9). Using Arndt's model (Ref. 21), an approximation for the rate of binding of Mg$^{2+}$ and with the adjusted rate constants, we have recreated the key features of the signal dynamics, mainly the timing of the peaks of polymerization, which closely match in both the simulation and the experiment.

In summary, the charge perturbation detection concept is based on the charge conservation principle and the induced surface charge of the polarizable electrode. As a result, the immobilized negative charge accumulated on the DNA backbone can be detected as soon as the positive proton leaves the detection zone, which occurs in a relatively short period. In principle, DNA synthesis confined to the detection zone could be detected without DNA immobilization, since the protons diffuse faster than the DNA molecules. The described label-free detection method can be easily applied to a multiple-electrode system and can provide rapid and sensitive detection of biological pathogens, genetic mutations or identification of unknown DNA sequences with a very small amount of sample. In addition, it also enables general measurements of enzymes undergoing similar catalytic reactions. The CPD electrode thus potentially represents a very robust and effective biosensor for many molecular and diagnostic applications.

Example 7

(FIGS. 6 and 7): Arrangement of CPD Devices into Detection Arrays

Figure 6:
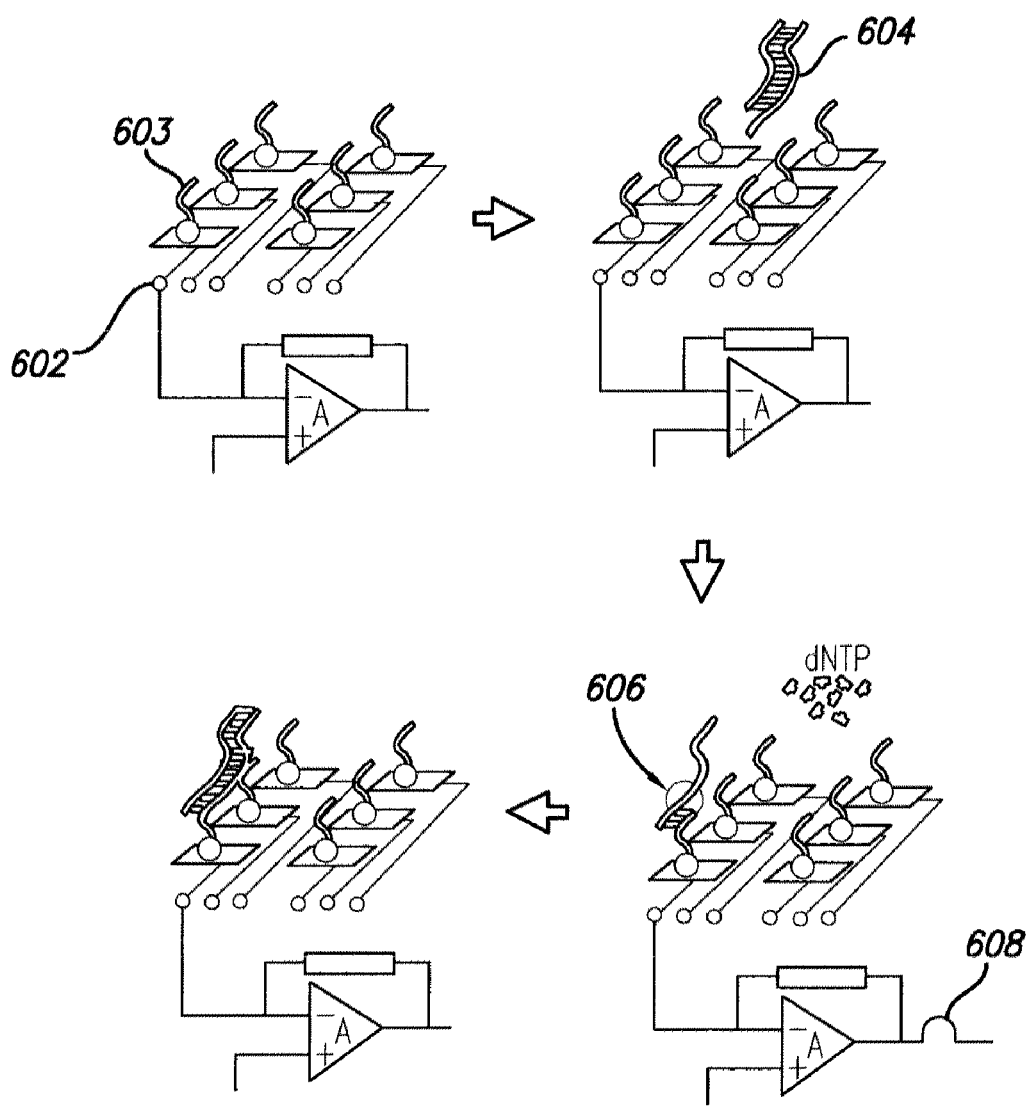
FIG. 6 is a diagram of a multiple electrode system useful for detecting pathogens.

Multi-electrode DNA detection can target a specific list of DNA sequences, such as for example DNA mutations of a pathogen. The concept is shown in FIG. 6. In the first panel, a series of leads 602 individually connect each of six electrodes to a detection circuit, comprising a sensitive voltage clamp circuit as described above. Each electrode has immobilized on it a single DNA strand (primer) 603 from a specific strain of human papilloma virus (HPV), e.g. HPV6 (electrode 1), HPV16 (electrode 2), HPV11 (electrode 3), HPV18 (electrode 4), HPV31 (electrode 5), and HPV45 (electrode 6). Appropriate DNA sequences to be immobilized as primers may be obtained from GenBank, e.g. Locus S73503, Locus HPV16R, Locus HPV 11R, etc., available through NCBI Entrez system, online. Locus identifications are as of the date of last modification listed in that entry as of the filing date of the present application. HPV is a double stranded DNA virus, whose entire genome has been sequenced. Over 80 strains of HPV are known.

In the second panel of FIG. 6, a sample DNA 604 with an exposed single strand DNA region from a sample containing HPV is added to the array. The sample should be at least partially denatured to allow DNA hybridization. In the third step, the sample has hybridized to the HPV immobilized DNA 603 and DNA polymerase enzyme 606 and dNTPs are added. In the fourth step, only the hybridized target is polymerizing and generating a signal 608.

Appropriate primers may be made by standard PCR protocol. Due to the sensitive nature of the present method, less than about 10 femtomol of primer is needed per electrode. However, more primers may be added to a single electrode to facilitate assembly.

In addition, multiple primers for different regions of DNA for a single target (e.g. different HPV6 genes) may be added to a single electrode to improve sensitivity. Multiple-electrode chips can find specific mutations in one-step run-off polymerization or by sequential dispensations and detection of individual nucleotides.

Figure 7:
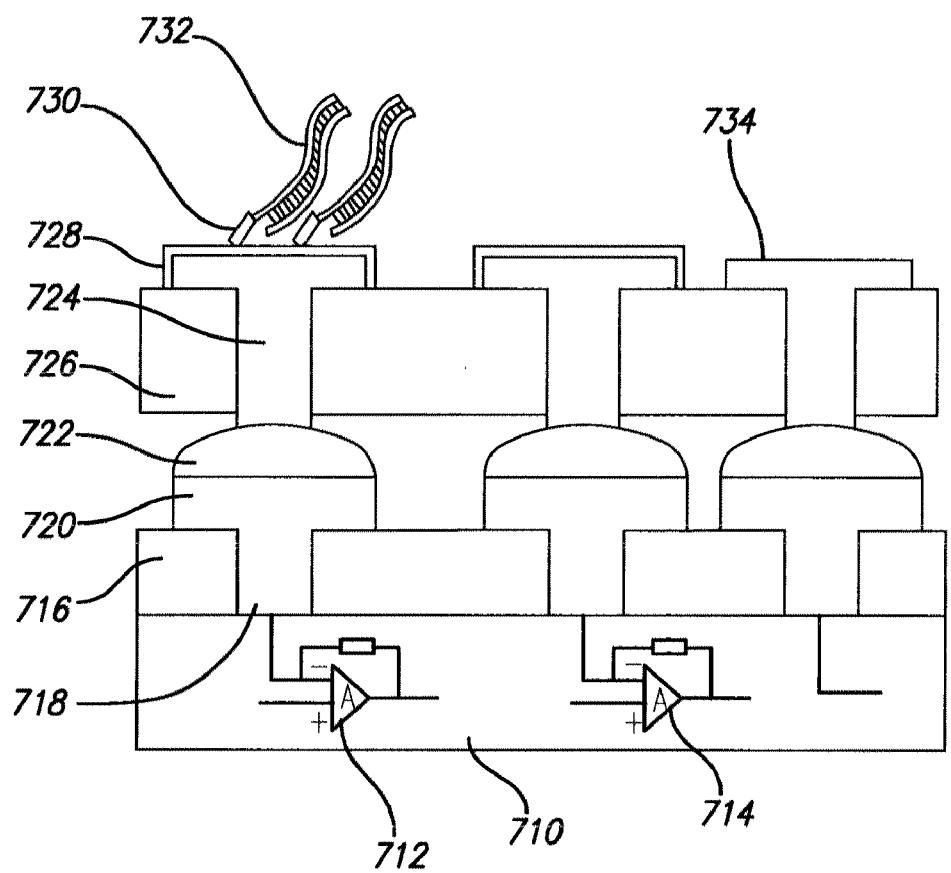
FIG. 7 is a schematic diagram of a CMOS chip implementation of the present system.

Referring now to FIG. 7, the present device may be integrated on a CMOS chip. A CMOS (complementary metal oxide semiconductor) semiconductor uses both NMOS (negative polarity) and PMOS (positive polarity) circuits. The chip 710 contains within it the differential amplifiers 712, 714 that are connected to each electrode. An insulating layer 716 contains connecting lines and vias 718 for connecting each electrode to an amplifier. A pad 720 is provided for a solder ball 722 to connect to an aluminum connector 724, which passes through a quartz or glass wafer 726. An electrode 728 of gold connects to the connector 724. The electrode has a chemical functionality 730 for immobilizing the test molecule (e.g. DNA) 732 to the electrode. A reference electrode 734 does not contain test molecules.

The electrode array is electrically connected via solder balls to the CMOS semiconductor chip. The electrode array is constructed on a quartz, glass or silicon wafer. The sensors, amplifiers and signal routing will be embedded in the CMOS chip and the output signal will be accessible via a pad and/or solder ball.

Example 8

(FIGS. 8-9): Integrated Designs

Figures 8A, 8B:
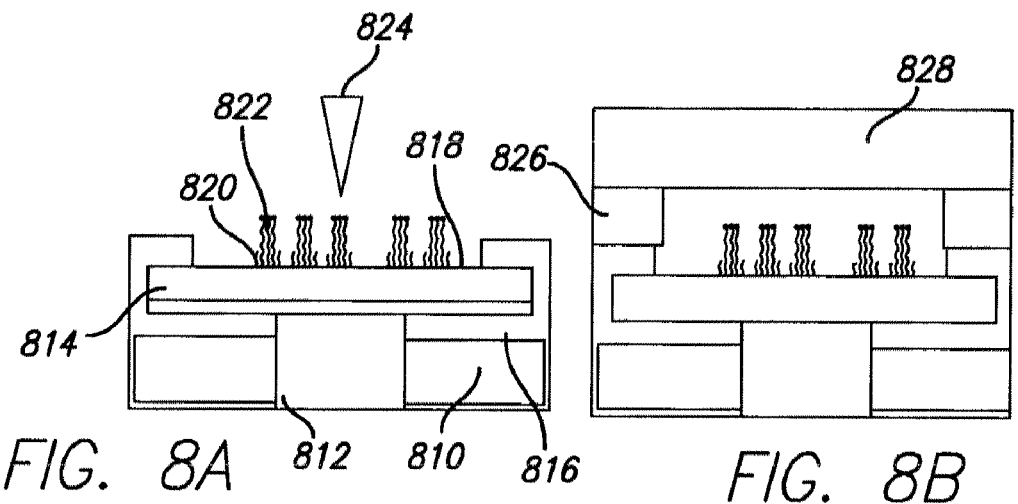
FIG. 8 is a diagrammatic side section view of an integrated charge perturbation device without a complete microfluidic channel (8A) and with a microfluidic channel (8B)
Figure 9:
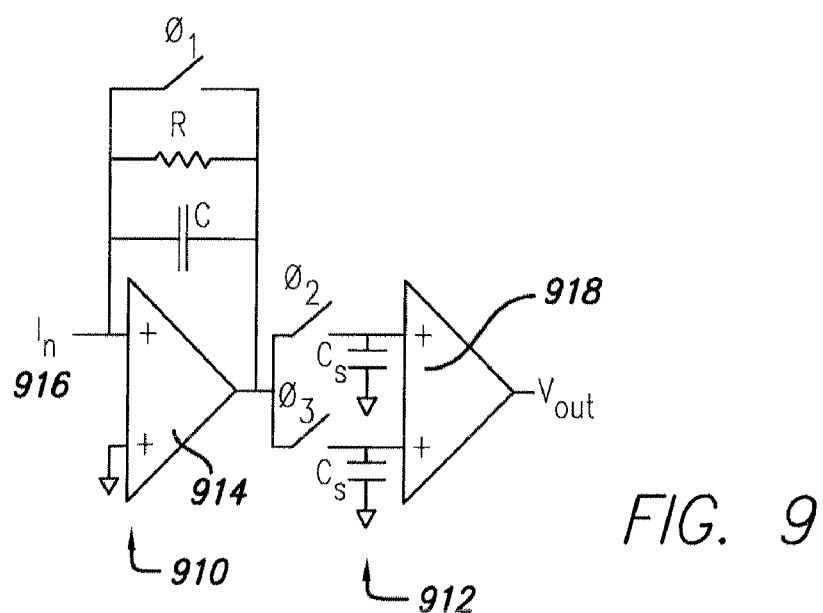
FIG. 9 is a diagram of a suitable low noise amplifier for use with an integrated charge perturbation device.

An exemplary integrated detection device is illustrated in FIGS. 8 and 9. This design implements further a design according to FIG. 7. This device can be used for parallel detection of DNA targets in an array format. The system presented here can detect low (femtomolar) amounts of DNA molecules, obviating the need for DNA amplification. It can be applied to the analysis of gene expression, short DNA sequencing, SNP detection, and pathogen detection.

When larger numbers of functional areas and a small device size is desired, one may use a modified microarray contact printer equipped with a digital camera and controlling software for precise solution delivery to the individual electrodes. Alignment of the contact pins with the electrodes will require some calibration and testing to ensure proper alignment. Testing may be done by optical image processing.

Another critical issue is the surface chemistry and attachment of the DNA. During the fabrication process, an oxide layer can form that prevents efficient attachment of the DNA oligonucleotides. Using electrical measurements of surface capacitance, as described above, one may determine the efficiency of attachment of the DNA-enzyme complex. Alternative methods include semi-manual dispensing of reagents by Piezo spray and XPS analysis to ensure that the chip is functional.

A microfluidic device according to the present invention may employ an automated method comprised of two components to accomplish a fast perfusion of buffer for equilibration and washing, and a more accurate dispensing of reagents.

The fast perfusion (~100 ms) of polymerization buffer in a desktop unit may be done with a Valvelink 8.2 controller and pinch valves (Automated Scientific Inc., CA), controlled by computer with an National Instruments (NI) 6225 board. The accurate injection (~10 ms) of 1-2 µl of dNTPs to the CPD electrode is performed with calibrated glass micropipettes connected to an eight-channel Micro Injector-Spritzer (BioScience Tools, CA) and positioned closely to the CPD electrode with a multi-electrode holder (BioScience Tools) and MM-33 micromanipulator.

For final assembly of the automated desktop system, the newly functionalized and tested chip will be connected to the reagent dispensing system. The chip will be placed in a prefabricated chip-holder that is connected to the multiple voltage-clamp amplifiers (Dagan, Inc.).

For sensor data acquisition, commercially available data acquisition boards and software packages from National Instruments are used. Their LabView software package can be used for any necessary processing on the PC. The NI 6225 board will be used. The NI 6225 can sample 16 single-ended channels at a rate of 15.6 kHz per channel. The board allows to be multiplexed so that up to 80 channels can be sampled at a rate of 3.1 kHz.

The DNA probe is first printed on the electrode chip and inserted into the device. The solution containing the target is added and allowed to hybridize to the probe (not shown). Then solution buffer (50 mM NaCl, 1.5 mM Mg), and DNA polymerase is introduced into the electrode chamber at the beginning of each measurement cycle. The individual dNTPs are dispensed sequentially (one dNTP per cycle) to the solution by using the fast perfusion/dispensation system. Transient ionic current signal in each cycle is detected using the voltage-clamp amplifier and digitized by computer acquisition board to produce the sequence polygram.

Microfluidic technology to deliver analytes and other small volumes of liquid can be adapted to a larger (e.g. an 8×8) biosensor array. The technology has sub-micron alignment precision of the microfluidic channels on top of the biosensor array. Furthermore, the microfluidic technology is compatible with materials that cannot withstand etching, elevated temperatures, or high electric fields.

Suitable microfluidic technology is formed of two layers and contains microfluidic channels interconnected with 8 parallel channels. Each channel runs over 8 sensors. The electrical wires and contacts are arrayed orthogonally to the microfluidic channels. The microfluidic channels may be designed to deliver the same mixture of reactants, or sequential reactants, to each electrode, or, with more fabrication, to provide individual channels for delivering different reactants to different electrodes.

Each of the 64 sensors can be measured independently. A thick top layer, fabricated by soft lithography from polydimethylsiloxane (PDMS) and backed by a transparent glass wafer, defines the larger microfluidic structures, such as inlet and outlet channels. Small microfluidic structures that would be difficult to create and align if they were included in the PDMS layer are instead defined in a thin layer of $SiO_2$, which has been deposited by ion beam deposition (IBD) and patterned by a lift-off process on top of the existing biosensor array. The combination of IBD and lift-off is compatible with the delicate biosensors and provides photolithographic alignment precision and feature definition of the channels in the $SiO_2$ layer. Moreover, the IBD-deposited $SiO_2$ layer provides spontaneous adhesion and sealing to the top PDMS layer and will accommodate a significant amount of substrate topography. Large channel overlaps between the two layers make the alignment of the top PDMS layer to the substrate error-tolerant. Finite element simulations are used to optimize the two-layer geometry for high analytic sensitivity and low flow impedance.

Microfluidic channels are formed as channels in parallel in one direction, e.g. from top to bottom of integrated device. Then, the electrodes to the sensor points would go from left to right. The sensor locations are at the intersection of the microfluidic channels and electrodes, forming an 8×8 array.

Fluidic channels down to approximately 2 um width have been created with good edge definition in a 250 nanometer thick $SiO_2$ layer, spanning 5 μm across a sensor area between intersections with larger channels in the PDMS layer.

Referring now to FIG. 8A, a cross section of a biochip is shown, after the $SiO_2$ channels are built on the chip and prior to DNA functionalization of the electrodes. A silicon substrate 810 has embedded therein an aluminum lead, which is part of a network of leads connecting individually each gold electrode in an array 814. The Si substrate 810 has an $SiO_2$ insulating layer 816, except for the exposed, functionalized portion 818. The exposed portion has an SAM 820. DNA molecules 822 are applied by a robotic dispenser or spotter 824.

DNA is applied at the wafer level by selecting a particular DNA solution for each electrode. Details of the biofunctionalization chemistry are described above.

For a compact charge perturbation device, the electrode size is preferably about 0.3 mm by 0.3 mm, which can be accommodated by existing assembly devices. The 0.3 mm electrode size can be scaled down to micrometer scale electrode with the use of semiconductor processing technology and microfluidics.

FIG. 8B shows the cross section of the biochip in 8A after sealing the DNA probes with PDMS channels 826 and illustrates how the electrodes for a CPD are integrated with microfluidics. The fabrication of precisely aligned microfluidic channels with micron-scale features on the electrodes has been simplified by combining the sealing and conformational benefits of PDMS soft lithography with the precision and durability of photolithographically patterned $SiO_2$. The biosensor-compatible microfabrication process provides reliable sealing on various substrate topographies. The tolerance in aligning the elastomeric PDMS layer to the substrate makes automation feasible, which should facilitate the development of inexpensive diagnostic biochips.

The microfluidic channel is sealed with a quartz sheet 828 on top of the PDMS layer 826. The channel is thus defined by a bottom surface containing DNA molecules adjacent an electrode; sidewalls comprising a deposited polymeric layer; and a top sheet confining liquid containing a sample to be analyzed and analytical reagents (e.g. polymerase, dNTPs, etc.) Two channels are illustrated in FIG. 8B.

An integrated circuit version of the CPD sensor using CMOS technology has several advantages over a version built from off-the-shelf components. First, it has increased detection sensitivity and increased signal-to-noise ratio because it can be optimized for low-noise operation. Second, it can be cheaper in volume production than a version built with off-the-shelf components. Third, it can be smaller than a version built with off-the-shelf components.

The signal-detection circuitry consists of two stages. The first stage is a voltage-clamp amplifier 910, which amplifies and converts current to voltage. The second stage 912 is used for output sampling in order to reduce noise. It performs a correlated double sampling of the first stage output. The correlated double sampling technique commonly used in digital cameras and in image sensor technology, cancels the low frequency 1/f noise, which is introduced by the first stage amplifier. Low frequency 1/f noise is inversely proportional to frequency so that the lower the frequency, the stronger the noise component. In commercial CMOS processes, the 1/f noise becomes equal to flat white noise in the kHz range. By canceling the 1/f noise with the correlated double-sampling technique, sensor sensitivity can be significantly improved by an order of magnitude.

The charge integrating amplifier 914 contains a ground and an input 916, along with a feed back resistor R, as is standard in voltage clamp amplifiers. The circuit further comprises a capacitor C for charge integration and a feed back switch $\Phi_1$. The output of the charge amplifier is input to either a positive or negative input to an amplifier 918. Switches $\Phi_2$ and $\Phi_3$ connect the charge amplifier to the differential amplifier. The switches $\Phi_{1-3}$ operate sequentially, i.e. one is on, then two is on, then three is on. This provides an over frequency to the output to be amplified, and, as explained above, lowers noise levels.

The amplifiers are designed using transistors in standard topologies and are optimized for low noise. Optimization of the charge-integrating amplifier circuit is possible after the impedance of the ssDNA-modified electrode is measured. Optimization will primarily consist of selection of the feedback impedance in the charge amplifier to maximize signal gain.

Integrated circuit design and verification software are indispensable parts of the design process. The basic software tools are schematic capture, parasitic extraction, circuit simulation, mask layout, and design verification. Industry-standard software is available for such uses, e.g. as provided by Cadence Design Systems for schematic capture, mask design, parasitic extraction, and design verification. The software HSpice may be used for circuit simulation.

Differential Amplifiers

The present devices utilize amplifiers that can detect small differences of charge at their inputs. The classic design for such an amplifier is the "voltage clamp" design illustrated here. An op-amp with no feedback (i.e. no resistors 24, 24a in FIG. 1) is already a differential amplifier, amplifying the voltage difference between the two inputs. However, its gain cannot be controlled, and it is generally too high to be of any practical use. The present application of negative feedback to op-amps has resulting in the practical loss of one of the inputs (e.g. the ground), the resulting amplifier is only good for amplifying a single voltage signal input. However, using known amplifier design principles, one can construct an op-amp circuit maintaining both voltage inputs, yet with a controlled gain set by external resistors. Other amplifiers and circuits may be constructed to allow for the control of the gain and sensitivity of the amplifier circuit. Buffer amplifiers are typically added to improve performance.

Example 9

Detection of Other Reactions

The sensitivity of the present CPD system enables the detection of other reactions besides DNA polymerization. Polymerization of other nucleic acids may also be detected in a sequence specific manner. The system may be used to detect binding of RNA to DNA, or double stranded RNA molecules found RNAi and ribozyme constructs. Furthermore, other biological molecular reactions generate more or less charged products, which can be detected using the described devices.

For example, the cleavage or unfolding of a polypeptide to expose charged arginine, lysine, histidine, aspartate, or glutamate residues may be detected. A protein may be immobilized on an electrode and a small amount of a protease and a potential protease inhibitor added, so that the effectiveness of a panel of protease inhibitors may be determined in numerous parallel reactions.

Molecules that act on phosphate groups may also be monitored by the present CPD system. This includes phosphotases and kinases. Measurable kinases include protein kinases, such as protein kinase C and serine/threonin kinsases, as well as pyruvate kinases, glycerol kinases and the like.

Other ATP dependent reactions measurable in the present system include that activity of DNA gyrase (which is modified by certain antibiotics) and the synthesis of glutathione (gamma-glu-cys-gly; GSH). GSH is usually present at high concentrations in most living cells, being the major reservoir of non-protein reduced sulfur. Because of its unique redox and nucleophilic properties, GSH serves in bio-reductive reactions as an important line of defense against reactive oxygen species, xenobiotics and heavy metals. GSH is synthesized from its constituent amino acids by two ATP-dependent reactions catalyzed by gamma-glutamylcysteine synthetase and glutathione synthetase.

Other enzymes, such as desulfurases (e.g. cysteine desulfurase), generate protons in solution and their activity will be detectible and measurable by the present devices. Sulfonucleotide reductases are a diverse family of enzymes that catalyze the first committed step of reductive sulfur assimilation. In this reaction, activated sulfate in the context of adenosine-phosphosulfate (APS) or -phosphoadenosine-phosphosulfate (PAPS) is converted to sulfite with reducing equivalents from thioredoxin. The sulfite generated in this reaction is utilized in bacteria and plants for the eventual production of essential biomolecules such as cysteine and coenzyme A. Humans do not possess a homologous metabolic pathway, and thus, these enzymes represent attractive targets for therapeutic intervention. Inhibitors of such enzymes could be added to wells containing one or more variants of such enzymes and their sulfate substrates and cofactors. Further details are given in Carroll K S, Gao H, Chen H, Stout C D, Leary J A, et al. (2005) "A Conserved Mechanism for Sulfonucleotide Reduction," PLoS Biol 3(8): e250.

Other applications for measurement of reactions with the present methods and apparatus include the measurement of the release or formation of phosphate drugs, such as pyrophosphate analogs, e.g. 4-amino-1 hydroxybutylidene bis-phosphonic acid monosodium salt (Fosamax®). Cell membranes containing ion channels may be attached to the electrodes, and the effect of test substances on ion permeability measured.

The present DNA sequencing reactions could also be repeated using the original templates, if the hybridized strand is denatured and washed away, leaving the target DNA. This would allow re-use of a device.

The present examples, methods, procedures, specific compounds and molecules are meant to exemplify and illustrate the invention and should in no way be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but would be understood by workers in the field. Such patents or publications are hereby incorporated by reference to the same extent as if each was specifically and individually incorporated by reference and for the purpose of describing and enabling the method or material referred to.

REFERENCES

1. Drummond, T. G., Hill, M. G. & Barton, J. K. Electrochemical DNA sensors. Nat Biotechnol 21, 1192-1199 (2003).
2. Fritz, J., Cooper, E. B., Gaudet, S., Sorger, P. K. & Manalis, S. R. Electronic detection of DNA by its intrinsic molecular charge. Proc Natl Acad Sci USA 99, 14142-14146 (2002).
3. Bockris, J. O. M., Modern electrochemistry 2A; Second edition. Fundamentals of Electrodics. Kluwer Academic Publishers: New York, 2001, 1558 pp.
4. Saddiku, M. N. O., Elements of Electromagnetics; Third edition. Oxford University Press: New York, 2001, 765 pp.
5. Steitz, T. A. et al. Two DNA polymerases: HIV reverse transcriptase and the Klenow fragment of *Escherichia coli* DNA polymerase I. Cold Spring Harb Symp Quant Biol 58, 495-504 (1993).
6. Fan, C., Plaxco, K. W. & Heeger, A. J. Biosensors based on binding-modulated donor-acceptor distances. Trends Biotechnol 23, 186-192 (2005).
7. Melamede, R. J. Automatable process for sequencing nucleotide. U.S. Pat. No. 4,863,849 (1985)
8. Ronaghi M, Uhlen M, Nyren P. A sequencing method based on real-time pyrophosphate. Science 281, 363-365 (1998).
9. Kuchta, R. D., Benkovic, P. & Benkovic, S. J. Kinetic mechanism whereby DNA polymerase I (Klenow) replicates DNA with high fidelity. Biochemistry 27, 6716-6725 (1988).

10. Johnson, K. A. Rapid quench kinetic analysis of polymerases, adenosinetriphosphatases, and enzyme intermediates. Methods Enzymol 249, 38-61 (1995).
11. Patel, S. S., Wong, I. & Johnson, K. A. Pre-steady-state kinetic analysis of processive DNA replication including complete characterization of an exonuclease-deficient mutant. Biochemistry 30, 511-525 (1991).
12. Sawaya, M. R., Prasad, R., Wilson, S. H., Kraut, J. & Pelletier, H. Crystal structures of human DNA polymerase beta complexed with gapped and nicked DNA: evidence for an induced fit mechanism. Biochemistry 36, 11205-11215 (1997).
13. Vanysek 1999 VANYSEK, P. (1999). Ionic conductivity and diffusion at infinite dilution. In CRC Handbook of Chemistry and Physics, 79th ed., section 5, Thermochemistry, electrochemistry and Kinetics, ed. LIDE, D. R., pp. 93-95. CRC Press, London.
14. Gutman, M. & Nachliel, E. Time-resolved dynamics of proton transfer in proteinous systems. Annu Rev Phys Chem 48, 329-356 (1997).
15. Georgievskii, Y., Medvedev, E. S. & Stuchebrukhov, A. A. Proton transport via the membrane surface. Biophys J 82, 2833-2846 (2002).
16. Wong, I., Patel, S. S. & Johnson, K. A. An induced-fit kinetic mechanism for DNA replication fidelity: direct measurement by single-turnover kinetics. Biochemistry 30, 526-537 (1991).
17. Davenport, R. J., Wuite, G. J., Landick, R. & Bustamante, C. Single-molecule study of transcriptional pausing and arrest by E. coli RNA polymerase. Science 287, 2497-2500 (2000).
18. Purohit, V., Grindley, N. D. & Joyce, C. M. Use of 2-aminopurine fluorescence to examine conformational changes during nucleotide incorporation by DNA polymerase I (Klenow fragment). Biochemistry 42, 10200-10211 (2003).
19. Zhong, X., Patel, S. S., Werneburg, B. G. & Tsai, M. D. DNA polymerase beta: multiple conformational changes in the mechanism of catalysis. Biochemistry 36, 11891-11900 (1997).
20. Dahlberg, M. E. & Benkovic, S. J. Kinetic mechanism of DNA polymerase I (Klenow fragment): identification of a second conformational change and evaluation of the internal equilibrium constant. Biochemistry 30, 4835-4843 (1991).
21. Arndt, J. W. et al. Insight into the catalytic mechanism of DNA polymerase beta: structures of intermediate complexes. Biochemistry 40, 5368-5375 (2001).
22. Ramanathan, S., Chary, K. V. & Rao, B. J. Incoming nucleotide binds to Klenow ternary complex leading to stable physical sequestration of preceding dNTP on DNA. Nucleic Acids Res 29, 2097-2105 (2001).
23. Kunkel, T. A. & Bebenek, K. DNA replication fidelity. Annu Rev Biochem 69, 497-529 (2000).
24. Allbritton N L, Meyer T, Stryer L. Range of messenger action of calcium ion and inositol 1,4,5-trisphosphate. Science. 1992 Dec. 11; 258(5089):1812-5.
25. Lan, S., Veiseh, M. & Zhang, M. Surface modification of silicon and gold-patterned silicon surfaces for improved biocompatibility and cell patterning selectivity. Biosens Bioelectron 20, 1697-1708 (2005).
26. Yuk, J. S. et al. Analysis of protein interactions on protein arrays by a wavelength interrogation-based surface plasmon resonance biosensor. Proteomics 4, 3468-3476 (2004).
27. Robinson, D. B. et al. DNA-functionalized MFe2O4 (M=Fe, Co, or Mn) nanoparticles and their hybridization to DNA-functionalized surfaces. Langmuir 21, 3096-3103 (2005).
28. Persson, H. H. J., Caseri, W. R., Suter, U. W. Versatile Method for Chemical Reactions with Self-Assembled Monolayers of Alkanethiols on Gold. Langmuir 17, 3643-3650 (2001).
29. Miyahara, J. The imaging plate: A new radiation imaging sensor. Chem. Today 223, 29-36 (1989).

What is claimed is:

1. A device for nucleic acid sequence detection, comprising:
    (a) a vessel for containing a reaction medium including at least one template nucleic acid molecule with components for template polymerization by complimentary addition of one or more nucleotides to the at least one template nucleic acid molecule with a concomitant proton release;
    (b) at least one polarizable electrode, connected to an amplifying circuit to amplify signals generated in response to polarity changes induced in the at least one polarizable electrode, so as to be sensitive to charge perturbations in the reaction medium whereby the polarity changes in the at least one electrode result in response to charge perturbations from the concomitant proton release as template polymerization of the at least one template nucleic acid molecule; and
    (c) a detection component, comprising the amplifying circuit, that generates signals in response to the polarity changes induced in the electrode, the signals indicating whether one or more corresponding nucleotides are added to the at least one template nucleic acid to thereby discern at least a portion of the at least one template nucleic acid sequence.

2. The device of claim 1 further comprising an insulating layer formed on the at least one polarizable electrode.

3. The device of claim 2 wherein the insulating layer comprises a self-assembled monolayer.

4. The device of claim 2 wherein the at least one template nucleic acid is linked to the insulating layer.

5. The device of claim 1 wherein the at least one amplifying circuit comprises a differential feedback amplifier.

6. The device of claim 1 wherein the at least one polarizable electrode comprises a metallic composition.

7. The device of claim 1 wherein the at least one polarizable electrode comprises an addressable array of polarizable electrodes.

8. The device of claim 1 wherein the at least one polarizable electrode comprises an integrated circuit formed on a semiconductor substrate.

* * * * *

```
                          SEQUENCE LISTING

<160> NUMBER OF SEQ ID NOS: 1

<210> SEQ ID NO 1
<211> LENGTH: 76
<212> TYPE: DNA
<213> ORGANISM: Artificial
<220> FEATURE:
<223> OTHER INFORMATION: 5' thiol modified synthetic DNA template

<400> SEQUENCE: 1
tttttttttt tttttttttt gctggaattc gtcagtgacg ccgtcgtttt acaacggaac    60
ggcagcaaaa tgttgc                                                    76
```